US00PP15646P2

(12) United States Plant Patent
Jorna

(10) Patent No.: US PP15,646 P2
(45) Date of Patent: Mar. 8, 2005

(54) ***IMPATIENS* PLANT NAMED 'TAMAR CHERRY RED'**

(50) Latin Name: *Impatiens hawkeri*
Varietal Denomination: Tamar Cherry Red

(75) Inventor: Anita Jorna, Maasland (NL)

(73) Assignee: Fides Goldstock Breeding B.V., DeLier (NL)

( * ) Notice: Subject to any disclaimer, the term of this patent is extended or adjusted under 35 U.S.C. 154(b) by 23 days.

(21) Appl. No.: 10/698,696

(22) Filed: Oct. 31, 2003

(51) Int. Cl.[7] ..... A01H 5/00
(52) U.S. Cl. ..... Plt./318
(58) Field of Search ..... Plt./318

*Primary Examiner*—Bruce R. Campell
*Assistant Examiner*—S. B. McCormick-Ewoldt
(74) *Attorney, Agent, or Firm*—Mark P. Bourgeois

(57) ABSTRACT

A new cultivar of *Impatiens* plant named 'Tamar Cherry Red' that is characterized by large deep red flowers, more branching, and earlier flowering. In combination, these traits set 'Tamar Cherry Red' apart from all other existing varieties of *Impatiens* known to the inventor.

1 Drawing Sheet

Botanical classification: *Impatiens hawkeri.*
Variety denomination: 'Tamar Cherry Red'.

BACKGROUND OF THE INVENTION

The present invention relates to a new and distinct cultivar of New Guinea *Impatiens* plant botanically known as *Impatiens hawkeri* and hereinafter referred to by the cultivar name 'Tamar Cherry Red'.

The new cultivar is the product of a breeding program conducted by the inventor in a cultivated area of De Lier, The Netherlands. The objective of the breeding program is to develop new *Impatiens* cultivars with interesting and unique flower and foliage colors.

'Tamar Cherry Red' is a hybrid that originated from the induced hybridization of the female or seed parent an unnamed proprietary seedling (not patented) and the male or pollen parent *Impatiens* 'Tamar Orange' (U.S. Plant Pat. No. 12,324). The cultivar 'Tamar Cherry Red' was selected by the inventor in 2000 as a single plant within the progeny of the stated cross in a controlled environment of De Lier, The Netherlands.

Asexual reproduction by terminal cuttings of the new cultivar 'Tamar Cherry Red' were taken in 2000 in De Lier, The Netherlands by the inventor. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Impatiens* cultivar 'Tamar Cherry Red'. These traits in combination distinguish 'Tamar Cherry Red' as a new and distinct cultivar apart from all other existing varieties of *Impatiens* known to the inventor.

1. *Impatiens* 'Tamar Cherry Red' exhibits deep red flowers.
2. *Impatiens* 'Tamar Cherry Red' exhibits flowers earlier.
3. *Impatiens* 'Tamar Cherry Red' exhibits more branching.

The closest comparison variety is *Impatiens* 'Martinique' (not patented). *Impatiens* 'Tamar Cherry Red' is different than 'Martinique' in having a faster flowering speed and a different flower color.

The new cultivar 'Tamar Cherry Red' is distinguishable from the female parent *Impatiens,* an unnamed proprietary seedling by the following characteristics:

1. 'Tamar Cherry Red' has larger flowers.
2. 'Tamar Cherry Red' has more branching.
3. 'Tamar Cherry Red' has darker red flowers, the flowers of the proprietary seedling are more pink.

The new cultivar 'Tamar Cherry Red' is distinguishable from the male parent *Impatiens* 'Tamar Orange' by the following characteristics:

1. 'Tamar Cherry Red' is less vigorous than 'Tamar Orange'.
2. 'Tamar Cherry Red' has smaller flowers than 'Tamar Orange'.
3. 'Tamar Cherry Red' has red flowers.

BRIEF DESCRIPTION OF THE DRAWING

The accompanying photograph illustrates the distinguishing traits of *Impatiens* 'Tamar Cherry Red'. The plant in the photograph shows an overall view of a 10 week old plant.

The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Impatiens* cultivar named 'Tamar Cherry Red'. Data was collected in De Lier, The Netherlands from 10 week glass greenhouse grown plants in 12 cm diameter containers. The time of year was June and the temperature was kept at 20° Centigrade during the day and night. The light level was natural outdoor light and there were no photoperiodic treatments or growth retardants used. Color determinations are in accordance with The Royal Horticultural Society Colour Chart 2001 edition, except where general color terms of ordinary dictionary significance are used. The growing requirements are similar to the species. 'Tamar Cherry Red' has not been tested under all possible conditions and phenotypic differences may be observed with variations in environmental, climatic, and cultural conditions, however, without any variance in genotype.

Botanical classification: *Impatiens* 'Tamar Cherry Red'.
Use: Ornamental.
Parentage: 'Tamar Cherry Red' is a hybrid plant that resulted from the induced hybridization of the following parent plants:
- *Female parent.*—*Impatiens* unnamed proprietary seedling.
- *Male parent.*—*Impatiens* 'Tamar Orange'.

Vigor: Moderate.
Growth rate: Approximately 7 cm. per month.
Growth habit: Broad Upright.
Plant shape: Rounded.
Suitable container size: 12 cm container.
Height: 19 cm. in height.
Width: 39 cm. in width.
Hardiness: USDA Zone 10.
Propagation: Terminal cuttings.
Time to initiate roots: Approximately 5 to 8 days to produce roots on an initial cutting.
Time to produce a rooted cutting or liner: Approximately 14–21 days.
Crop time: From a rooted cutting, approximately 9 weeks are required to produce a finished flowering plant.
Root system: Fine and fibrous.
Stem:
- *Branching habit.*—Basal branching and lateral branches.
- *Average number of lateral branches.*—7.
- *Pinching.*—Yes.
- *Lateral branch diameter.*—8 mm. in diameter.
- *Lateral branch length.*—15 cm. in length.
- *Lateral branch strength.*—Moderately strong.
- *Stem color.*—178A.
- *Pubescence.*—Absent.
- *Internode length.*—6.1 cm. between nodes.
- *Shape.*—Round.
- *Surface.*—Glabrous, slightly glossy.

Foliage:
- *Texture.*—Both sides moderately glossy.
- *Leaf arrangement.*—Whorled, 5 per whorl.
- *Compound or single.*—Single.
- *Quantity of leaves per lateral branch.*—20.
- *Leaf shape.*—Elliptic.
- *Leaf apex.*—Acute.
- *Leaf base.*—Attenuate.
- *Leaf length.*—12 cm. in length.
- *Leaf width.*—4.2 cm. in width.
- *Pubescence.*—Absent.
- *Leaf margin.*—Serrate.
- *Vein pattern.*—Pinnate.
- *Young leaf color* (*lower surface*).—Between 138A and 191A.
- *Young leaf color* (*upper surface*).—Between 139A and 147A.
- *Mature leaf color* (*lower surface*).—147B.
- *Mature leaf color* (*upper surface*).—Between 139A and 147A.
- *Vein color* (*lower surface*).—182A.
- *Vein color* (*upper surface*).—195B.
- *Leaf attachment.*—Petiolate.
- *Petiole dimensions.*—4.9 cm in length and 3.0 mm. in width.
- *Petiole color upper side.*—195B.
- *Petiole color lower side.*—182A.

Flower:
- *Flower arrangement.*—Solitary, axillary flowers.
- *Inflorescence type.*—Solitary.
- *Flowering habit.*—Continuous.
- *Quantity of flowers per lateral stem.*—Approximately 20.
- *Quantity of flower buds per lateral stem.*—Approximately 20.
- *Quantity of flowers and buds per plant.*—Approximately 250.
- *Flowering season.*—Spring to summer.
- *Rate of flower opening.*—Approximately 10% of the flowers are opened at once.
- *Fragrance.*—None.
- *Flower bud length.*—1.2 cm. in length.
- *Flower bud diameter.*—7 mm. in diameter.
- *Flower bud shape.*—Ovate.
- *Bud color.*—145B with tints of red 46A.
- *Rate of bud opening.*—6 days.
- *Flower aspect.*—Outward.
- *Flower shape.*—Irregular, flowers somewhat cupped and rounded rectangular in shape.
- *Flower dimensions.*—5.0 cm. in diameter and 1.8 cm. in height.
- *Flower longevity.*—Lasts approximately 10 days on plant.
- *Petal appearance.*—Dull.
- *Petal texture.*—Glabrous.
- *Petal arrangement.*—Irregular.
- *Number of petals.*—Five in number.
- *Petals fused or unfused.*—Unfused.
- *Petal shape.*—Banner petal: Reniform, lateral petals: Broad obcordate.
- *Petal margin.*—Entire.
- *Petal apex.*—Banner petal: Rounded, lateral petal: Retuse.
- *Petal dimensions.*—Banner petal: 2.4 cm. In length, 3.4 cm. in width, lateral petal: 2.6 cm. in length and 2.6 cm. in width.
- *Banner petal color when opening* (*upper side*).—53A.
- *Lateral petal color when opening* (*upper side*).—53A.
- *Banner petal color when opening* (*under side*).—53B with a yellow-green central band 146B.
- *Lateral petal color when opening* (*under side*).—53B.
- *Banner petal color fully open* (*upper side*).—53A.
- *Lateral petal color fully open* (*upper side*).—53A.
- *Banner petal color fully open* (*under side*).—53B with a yellow-green central band 146B.
- *Lateral petal color fully open* (*under side*).—53B with a small basal spot 58A.
- *Petaloids.*—Absent.

Self-cleaning or persistent: Self-cleaning.
Spur length: About 4.6 cm.
Spur texture: Smooth, glabrous.
Spur color: 185A.
Sepals:
- *Sepal arrangement.*—One spurred lower sepals located between two side sepals.
- *Sepal color immature* (*upper side*).—145B.
- *Sepal color immature* (*under side*).—145B.

*Sepal color mature* (*upper side*).—Lower spur sepal 53C with a base 57D, side sepals 145A.

*Sepal color mature* (*under side*).—Lower spur sepal 54C with a red margin 53C, side sepals 145A.

*Sepal surface.*—Dull.

*Number of sepals.*—Three.

*Sepal shape.*—Lower spur sepal broad ovate with spur, side sepals ovate.

*Sepal margin.*—Entire.

*Sepal apex.*—Apiculate.

*Sepal base.*—Cuneate.

*Sepal dimensions.*—Lower spurred sepal 1.4 cm. in length and 1 cm. in width, side sepals 1.3 cm. in length and 5 mm. in width.

Pedicels:

*Pedicel dimensions.*—6.9 cm. in length and 1.5 mm. in diameter.

*Pedicel angle.*—45°.

*Pedicel color.*—144A.

*Pedicel strength.*—Moderate.

Reproduction organs:

*Stamen number.*—5.

*Anther shape.*—Introrse and fused into a cap over the ovary.

*Anther dimensions.*—2 mm. In length and 2 mm. in width.

*Anther color.*—182D.

*Amount of pollen.*—Low.

*Pollen color.*—158D.

*Pistil number.*—1 in number.

*Pistil dimensions.*—1 mm. in length.

*Stigma shape.*—Capitate.

*Stigma color.*—145C.

*Style.*—Not visible.

*Ovary color.*—143B.

Seed: Seed production has not been observed.

Disease resistance: Plants of the new *Impatiens* have not been observed for disease resistance.

It is claimed:

1. A new and distinct variety of *Impatiens* plant named 'Tamar Cherry Red' as described and illustrated.

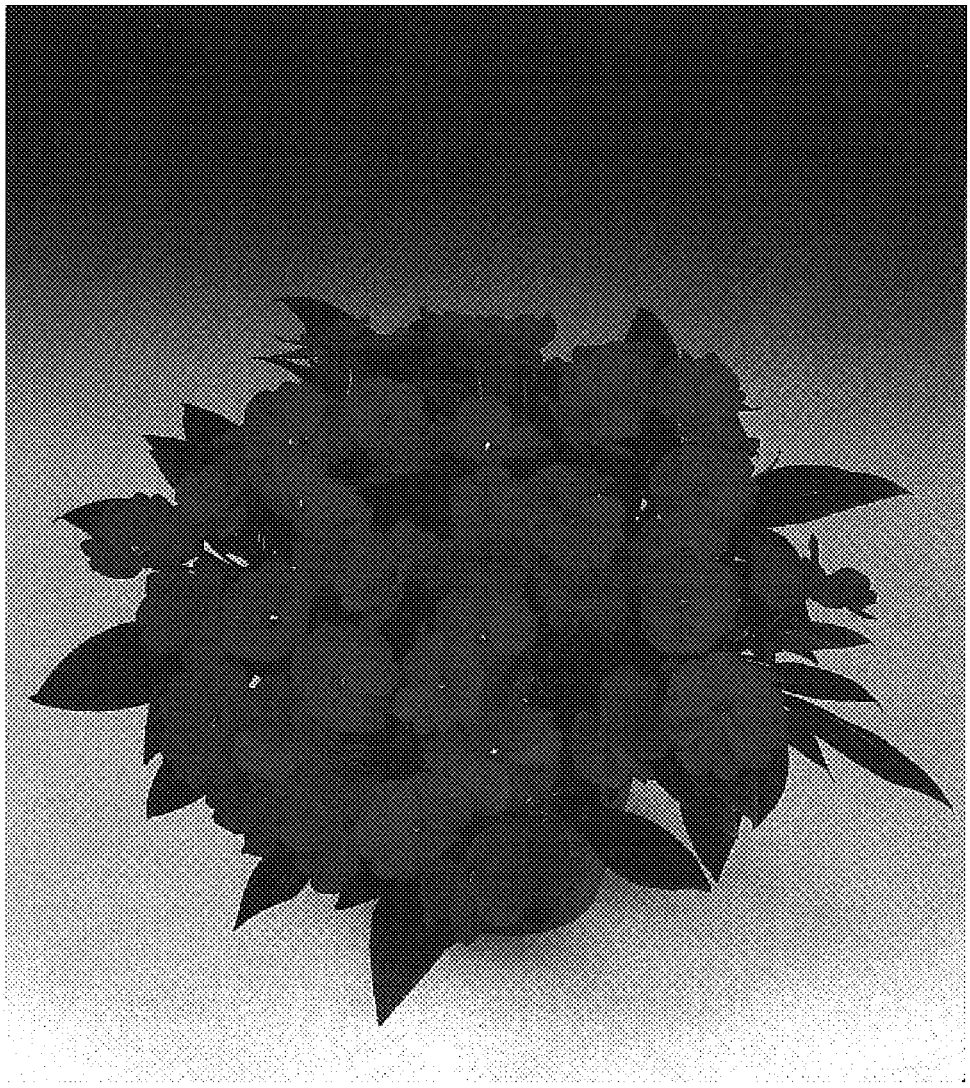

* * * * *